(12) United States Patent
Miller et al.

(10) Patent No.: US 7,744,606 B2
(45) Date of Patent: Jun. 29, 2010

(54) MULTI-LUMEN INSTRUMENT GUIDE

(75) Inventors: Thomas I. Miller, Palm Bay, FL (US); James G. Skakoon, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 489 days.

(21) Appl. No.: 11/005,605

(22) Filed: Dec. 4, 2004

(65) Prior Publication Data
US 2006/0122627 A1     Jun. 8, 2006

(51) Int. Cl.
*A61B 19/00*     (2006.01)

(52) U.S. Cl. ..................... 606/130

(58) Field of Classification Search ............ 606/130, 606/96, 98, 87, 102; 408/75; 600/429; D11/3, D11/6, 11; 411/1, 2, 427, 436, 437
See application file for complete search history.

(56) References Cited

U.S. PATENT DOCUMENTS

| | | |
|---|---|---|
| 431,187 A | 7/1890 | Foster |
| 438,801 A | 10/1890 | Delehanty |
| 873,009 A | 12/1907 | Baxter |
| 1,129,333 A | 2/1915 | Clarke |
| 1,664,210 A | 3/1928 | Hall |
| 2,119,649 A | 6/1938 | Roosen |
| 2,135,160 A | 11/1938 | Beekhuis |
| 2,497,820 A | 2/1950 | Kielland |
| 2,686,890 A | 8/1954 | Davis |
| 3,010,347 A | 11/1961 | Kron |
| 3,016,899 A | 1/1962 | Stenvall |
| 3,017,887 A | 1/1962 | Heyer |
| 3,055,370 A | 9/1962 | McKinney et al. |
| 3,055,371 A | 9/1962 | Kulick, G., et al. |
| 3,115,140 A | 12/1963 | Volkman |
| 3,135,263 A | 6/1964 | Connelley Jr. |

(Continued)

FOREIGN PATENT DOCUMENTS

DE     3108766     9/1982

(Continued)

OTHER PUBLICATIONS

International Search Report and Written Opinion for PCT/US05/43651 mailed May 8, 2008.

(Continued)

*Primary Examiner*—Anhtuan T Nguyen
*Assistant Examiner*—Ryan J Severson
(74) *Attorney, Agent, or Firm*—Scott A. Marks; Stephen W. Bauer

(57) ABSTRACT

This document discusses, among other things, a method of manufacture including a mold having at least one pin, and surrounding the pin with a hardenable material to form a first guide layer. The mold and pin are removed from the resulting first guide layer, to define a substantially untapered first instrument passage that corresponds to the geometry of the pin. Optionally, the first instrument passage includes at least five substantially untapered channels including a central channel. The first instrument passage is aligned with a substantially untapered second instrument passage of a stacked second guide layer. In a further example, the first and second guide layers are coupled to a guide coupler that cooperatively aligns the first and second instrument passages. The guide layers can be used with a trajectory guide for image guided surgery.

28 Claims, 6 Drawing Sheets

U.S. PATENT DOCUMENTS

| | | | |
|---|---|---|---|
| 3,223,087 A | 12/1965 | Vladyka et al. | |
| 3,262,452 A * | 7/1966 | Hardy et al. | 606/130 |
| 3,273,559 A | 9/1966 | Evans | |
| 3,282,152 A | 11/1966 | Myer | |
| 3,402,710 A | 9/1968 | Paleschuck | |
| 3,444,861 A | 5/1969 | Schulte | |
| 3,457,922 A | 7/1969 | Ray | |
| 3,460,537 A | 8/1969 | Zeis | |
| 3,508,552 A | 4/1970 | Hainault | |
| 3,672,352 A | 6/1972 | Summers | |
| 3,760,811 A | 9/1973 | Andrew et al. | |
| 3,817,249 A | 6/1974 | Nicholson | |
| 3,893,449 A | 7/1975 | Lee et al. | |
| 3,981,079 A | 9/1976 | Lenczycki | |
| 4,013,080 A | 3/1977 | Froning | |
| 4,026,276 A | 5/1977 | Chubbuck | |
| 4,040,427 A | 8/1977 | Winnie | |
| 4,131,257 A | 12/1978 | Sterling | |
| 4,230,117 A | 10/1980 | Anichkov et al. | |
| 4,265,252 A | 5/1981 | Chubbuck et al. | |
| 4,312,337 A | 1/1982 | Donohue | |
| 4,318,401 A | 3/1982 | Zimmerman | |
| 4,328,813 A | 5/1982 | Ray | |
| 4,341,220 A | 7/1982 | Perry | |
| 4,345,606 A | 8/1982 | Littleford | |
| 4,350,159 A | 9/1982 | Gouda | |
| 4,355,645 A | 10/1982 | Mitani et al. | |
| 4,386,602 A | 6/1983 | Sheldon et al. | |
| 4,418,894 A | 12/1983 | Mailliet et al. | |
| 4,448,195 A | 5/1984 | LeVeen et al. | |
| 4,463,758 A | 8/1984 | Patil et al. | |
| 4,475,550 A | 10/1984 | Bremer et al. | |
| 4,483,344 A | 11/1984 | Atkov et al. | |
| 4,571,750 A | 2/1986 | Barry | |
| 4,572,198 A | 2/1986 | Codrington | |
| 4,579,120 A | 4/1986 | MacGregor | |
| 4,592,352 A | 6/1986 | Patil | |
| 4,598,708 A | 7/1986 | Beranek | |
| 4,608,977 A | 9/1986 | Brown | |
| 4,617,925 A | 10/1986 | Laitinen | |
| 4,618,978 A | 10/1986 | Cosman | |
| 4,629,451 A | 12/1986 | Winters et al. | |
| 4,638,798 A | 1/1987 | Shelden et al. | |
| 4,660,563 A | 4/1987 | Lees | |
| 4,665,928 A | 5/1987 | Linial et al. | |
| 4,699,616 A | 10/1987 | Nowak et al. | |
| 4,705,436 A | 11/1987 | Robertson et al. | |
| 4,706,665 A | 11/1987 | Gouda | |
| 4,733,661 A | 3/1988 | Palestrant | |
| 4,755,642 A | 7/1988 | Parks | |
| 4,791,934 A | 12/1988 | Brunnett | |
| 4,793,355 A | 12/1988 | Crum et al. | |
| 4,798,208 A | 1/1989 | Faasse, Jr. | |
| 4,805,615 A * | 2/1989 | Carol | 606/130 |
| 4,805,634 A | 2/1989 | Ullrich et al. | |
| 4,807,620 A | 2/1989 | Strul et al. | |
| 4,809,694 A | 3/1989 | Ferrara | |
| 4,824,436 A | 4/1989 | Wolinsky | |
| 4,826,487 A | 5/1989 | Winter | |
| 4,869,247 A | 9/1989 | Howard, III et al. | |
| 4,883,053 A | 11/1989 | Simon | |
| 4,896,673 A | 1/1990 | Rose et al. | |
| 4,902,129 A | 2/1990 | Siegmund et al. | |
| 4,922,924 A | 5/1990 | Gambale et al. | |
| 4,955,891 A | 9/1990 | Carol | |
| 4,957,481 A | 9/1990 | Gatenby | |
| 4,986,280 A | 1/1991 | Marcus et al. | |
| 4,986,281 A | 1/1991 | Preves et al. | |
| 4,989,608 A | 2/1991 | Ratner | |
| 4,991,579 A | 2/1991 | Allen | |
| 4,998,938 A | 3/1991 | Ghajar et al. | |
| 5,006,122 A | 4/1991 | Wyatt et al. | |
| 5,024,236 A | 6/1991 | Shapiro | |
| 5,027,818 A | 7/1991 | Bova et al. | |
| 5,030,223 A | 7/1991 | Anderson et al. | |
| 5,050,608 A | 9/1991 | Watanabe et al. | |
| 5,052,329 A | 10/1991 | Bennett | |
| 5,054,497 A | 10/1991 | Kapp et al. | |
| 5,057,084 A | 10/1991 | Ensminger et al. | |
| 5,057,106 A | 10/1991 | Kasevich et al. | |
| 5,065,761 A | 11/1991 | Pell | |
| 5,078,140 A | 1/1992 | Kwoh | |
| 5,078,142 A | 1/1992 | Siczek et al. | |
| 5,080,662 A | 1/1992 | Paul | |
| 5,087,256 A | 2/1992 | Taylor et al. | |
| 5,099,846 A | 3/1992 | Hardy | |
| 5,102,402 A | 4/1992 | Dror et al. | |
| 5,116,344 A | 5/1992 | Sundqvist et al. | |
| 5,116,345 A | 5/1992 | Jewell et al. | |
| 5,120,322 A | 6/1992 | Davis et al. | |
| 5,125,888 A | 6/1992 | Howard et al. | |
| 5,142,930 A | 9/1992 | Allen et al. | |
| 5,143,086 A | 9/1992 | Duret et al. | |
| 5,154,179 A | 10/1992 | Ratner | |
| 5,154,723 A | 10/1992 | Kubota et al. | |
| 5,163,430 A | 11/1992 | Carol | |
| 5,166,875 A | 11/1992 | Machida et al. | |
| 5,171,217 A | 12/1992 | March et al. | |
| 5,174,297 A | 12/1992 | Daikuzono et al. | |
| 5,186,174 A | 2/1993 | Schlondorff et al. | |
| 5,201,742 A | 4/1993 | Hasson | |
| 5,207,223 A | 5/1993 | Adler | |
| 5,207,688 A | 5/1993 | Carol | |
| 5,211,165 A | 5/1993 | Dumoulin et al. | |
| 5,221,264 A | 6/1993 | Wilk et al. | |
| 5,222,499 A | 6/1993 | Allen et al. | |
| 5,230,338 A | 7/1993 | Allen et al. | |
| 5,230,623 A | 7/1993 | Guthrie et al. | |
| 5,242,415 A | 9/1993 | Kantrowitz et al. | |
| 5,246,448 A | 9/1993 | Chang | |
| 5,257,998 A | 11/1993 | Ota et al. | |
| 5,263,939 A | 11/1993 | Wortrich | |
| 5,263,956 A | 11/1993 | Nobles | |
| 5,267,970 A | 12/1993 | Chin et al. | |
| 5,269,305 A | 12/1993 | Corol | |
| 5,279,309 A | 1/1994 | Taylor et al. | |
| 5,279,575 A | 1/1994 | Sugarbaker | |
| 5,280,427 A | 1/1994 | Magnusson et al. | |
| 5,290,266 A | 3/1994 | Rohling et al. | |
| 5,291,890 A | 3/1994 | Cline et al. | |
| 5,300,080 A | 4/1994 | Clayman et al. | |
| 5,305,203 A | 4/1994 | Raab et al. | |
| 5,306,272 A | 4/1994 | Cohen et al. | |
| 5,309,913 A | 5/1994 | Kormos et al. | |
| 5,330,485 A | 7/1994 | Clayman et al. | |
| 5,354,283 A | 10/1994 | Bark et al. | |
| 5,361,763 A | 11/1994 | Kao et al. | |
| 5,366,446 A | 11/1994 | Tal et al. | |
| 5,375,588 A | 12/1994 | Yoon | |
| 5,375,596 A | 12/1994 | Twiss et al. | |
| 5,380,302 A | 1/1995 | Orth | |
| 5,383,454 A | 1/1995 | Bucholz | |
| 5,387,220 A | 2/1995 | Pisharodi | |
| 5,394,457 A | 2/1995 | Leibinger et al. | |
| 5,405,330 A | 4/1995 | Zunitch et al. | |
| 5,423,832 A | 6/1995 | Gildenberg | |
| 5,423,848 A | 6/1995 | Washizuka et al. | |
| 5,445,166 A | 8/1995 | Taylor | |
| 5,452,720 A | 9/1995 | Smith et al. | |
| 5,464,446 A | 11/1995 | Dreessen et al. | |
| 5,470,307 A | 11/1995 | Lindall | |
| 5,474,564 A | 12/1995 | Clayman et al. | |
| 5,483,961 A | 1/1996 | Kelly et al. | |
| 5,494,034 A | 2/1996 | Schlondorff et al. | |

| | | | |
|---|---|---|---|
| 5,494,655 A | 2/1996 | Rocklage et al. | |
| 5,515,160 A | 5/1996 | Schulz et al. | |
| 5,517,990 A | 5/1996 | Kalfas et al. | |
| 5,528,652 A | 6/1996 | Smith et al. | |
| 5,541,377 A * | 7/1996 | Stuhlmacher | 200/296 |
| 5,572,905 A * | 11/1996 | Cook, Jr. | 74/411 |
| 5,572,999 A | 11/1996 | Funda et al. | |
| 5,575,798 A * | 11/1996 | Koutrouvelis | 606/130 |
| 5,618,288 A | 4/1997 | Calvo et al. | |
| 5,622,170 A | 4/1997 | Schulz | |
| 5,638,819 A | 6/1997 | Manwaring et al. | |
| 5,639,276 A | 6/1997 | Weinstock et al. | |
| 5,643,286 A | 7/1997 | Warner et al. | |
| 5,647,361 A | 7/1997 | Damadian | |
| 5,649,936 A | 7/1997 | Real | |
| 5,658,272 A | 8/1997 | Hasson | |
| 5,662,600 A | 9/1997 | Watson et al. | |
| 5,667,514 A | 9/1997 | Heller | |
| 5,695,501 A | 12/1997 | Carol et al. | |
| 5,713,858 A | 2/1998 | Heruth et al. | |
| 5,755,697 A | 5/1998 | Jones et al. | |
| 5,776,064 A | 7/1998 | Kalfas et al. | |
| 5,776,143 A * | 7/1998 | Adams | 606/130 |
| 5,776,144 A | 7/1998 | Leysieffer et al. | |
| 5,788,713 A * | 8/1998 | Dubach et al. | 606/130 |
| 5,807,033 A | 9/1998 | Benway | |
| 5,809,694 A | 9/1998 | Postans et al. | |
| 5,810,712 A | 9/1998 | Dunn | |
| 5,817,106 A | 10/1998 | Real | |
| 5,823,975 A | 10/1998 | Stark et al. | |
| 5,833,627 A | 11/1998 | Shmulewitz et al. | |
| 5,843,150 A | 12/1998 | Dreessen et al. | |
| 5,851,183 A | 12/1998 | Bucholz | |
| 5,865,817 A | 2/1999 | Moenning et al. | |
| 5,865,842 A | 2/1999 | Knuth et al. | |
| 5,871,445 A | 2/1999 | Bucholz | |
| 5,871,487 A | 2/1999 | Warner et al. | |
| 5,873,822 A | 2/1999 | Ferre et al. | |
| 5,891,034 A | 4/1999 | Bucholz | |
| 5,891,157 A | 4/1999 | Day et al. | |
| 5,927,277 A | 7/1999 | Baudino et al. | |
| 5,950,629 A | 9/1999 | Taylor et al. | |
| 5,954,687 A | 9/1999 | Baudino | |
| 5,957,933 A | 9/1999 | Yanof et al. | |
| 5,957,934 A | 9/1999 | Rapoport et al. | |
| 5,964,705 A | 10/1999 | Truwit et al. | |
| 5,980,535 A | 11/1999 | Barnett et al. | |
| 5,984,930 A | 11/1999 | Maciunas et al. | |
| 5,993,463 A | 11/1999 | Truwit | |
| 5,997,471 A | 12/1999 | Gumb et al. | |
| 6,006,126 A | 12/1999 | Cosman | |
| 6,018,094 A | 1/2000 | Fox | |
| 6,021,343 A | 2/2000 | Foley et al. | |
| 6,024,729 A | 2/2000 | Dehdashtian et al. | |
| 6,030,223 A | 2/2000 | Sugimori | |
| 6,039,725 A | 3/2000 | Moenning et al. | |
| 6,042,540 A | 3/2000 | Johnston et al. | |
| 6,044,304 A | 3/2000 | Baudino | |
| 6,058,323 A | 5/2000 | Lemelson | |
| 6,071,288 A | 6/2000 | Carol et al. | |
| 6,076,008 A | 6/2000 | Bucholz | |
| 6,079,681 A | 6/2000 | Stern et al. | |
| 6,110,182 A | 8/2000 | Mowlai-Ashtiani | |
| 6,117,143 A | 9/2000 | Hynes et al. | |
| 6,120,465 A | 9/2000 | Guthrie et al. | |
| 6,135,946 A | 10/2000 | Konen et al. | |
| 6,179,826 B1 | 1/2001 | Aebischer et al. | |
| 6,195,577 B1 | 2/2001 | Truwit et al. | |
| 6,206,890 B1 | 3/2001 | Truwit | |
| 6,210,417 B1 | 4/2001 | Baudino et al. | |
| 6,231,526 B1 | 5/2001 | Taylor et al. | |
| 6,236,875 B1 | 5/2001 | Bucholz et al. | |
| 6,238,402 B1 | 5/2001 | Sullivan, III et al. | |
| 6,254,532 B1 | 7/2001 | Paolitto et al. | |
| 6,257,407 B1 | 7/2001 | Truwit et al. | |
| 6,261,300 B1 | 7/2001 | Carol et al. | |
| 6,267,769 B1 | 7/2001 | Truwit | |
| 6,267,770 B1 | 7/2001 | Truwit | |
| 6,273,896 B1 | 8/2001 | Franck et al. | |
| 6,282,437 B1 | 8/2001 | Franck et al. | |
| 6,290,644 B1 | 9/2001 | Green, II et al. | |
| 6,298,262 B1 | 10/2001 | Franck et al. | |
| 6,315,770 B1 | 11/2001 | de la Torre et al. | |
| 6,321,104 B1 | 11/2001 | Gielen et al. | |
| 6,327,491 B1 | 12/2001 | Franklin et al. | |
| 6,356,792 B1 | 3/2002 | Errico et al. | |
| 6,368,329 B1 | 4/2002 | Truwit | |
| 6,400,992 B1 | 6/2002 | Borgersen et al. | |
| 6,457,963 B1 | 10/2002 | Tawara et al. | |
| 6,482,182 B1 | 11/2002 | Carroll et al. | |
| 6,488,620 B1 | 12/2002 | Segermark et al. | |
| 6,491,699 B1 | 12/2002 | Henderson et al. | |
| 6,529,765 B1 | 3/2003 | Franck et al. | |
| 6,537,232 B1 | 3/2003 | Kucharczyk et al. | |
| 6,546,277 B1 | 4/2003 | Franck et al. | |
| 6,546,279 B1 | 4/2003 | Bova et al. | |
| 6,547,795 B2 | 4/2003 | Schneiderman | |
| 6,556,857 B1 | 4/2003 | Estes et al. | |
| 6,609,020 B2 | 8/2003 | Gill et al. | |
| 6,610,100 B2 * | 8/2003 | Phelps et al. | 623/23.7 |
| 6,632,184 B1 | 10/2003 | Truwit | |
| 6,655,014 B1 | 12/2003 | Babini | |
| 6,662,035 B2 | 12/2003 | Sochor | |
| 6,676,669 B2 | 1/2004 | Charles et al. | |
| 6,706,050 B1 * | 3/2004 | Giannadakis | 606/185 |
| 6,726,678 B1 | 4/2004 | Nelson et al. | |
| 6,746,471 B2 | 6/2004 | Mortier et al. | |
| 6,752,812 B1 | 6/2004 | Truwit | |
| 6,765,122 B1 | 7/2004 | Stout | |
| 6,773,443 B2 | 8/2004 | Truwit et al. | |
| 6,782,288 B2 | 8/2004 | Truwit et al. | |
| 6,802,323 B1 | 10/2004 | Truwit et al. | |
| 6,902,569 B2 | 6/2005 | Parmer et al. | |
| 6,913,478 B2 | 7/2005 | Lamirey | |
| 6,944,895 B2 | 9/2005 | Truwit | |
| 6,960,216 B2 | 11/2005 | Kolb et al. | |
| 7,204,840 B2 | 4/2007 | Skakoon et al. | |
| 7,479,146 B2 | 1/2009 | Malinowski | |
| 2001/0014771 A1 | 8/2001 | Truwit et al. | |
| 2001/0027271 A1 | 10/2001 | Franck et al. | |
| 2001/0037524 A1 | 11/2001 | Truwit | |
| 2002/0010479 A1 | 1/2002 | Skakoon et al. | |
| 2002/0019641 A1 | 2/2002 | Truwit | |
| 2002/0022847 A1 * | 2/2002 | Ray et al. | 606/96 |
| 2002/0052610 A1 | 5/2002 | Skakoon et al. | |
| 2002/0077646 A1 | 6/2002 | Truwit et al. | |
| 2002/0156372 A1 | 10/2002 | Skakoon et al. | |
| 2003/0079287 A1 | 5/2003 | Truwit | |
| 2003/0187351 A1 | 10/2003 | Franck et al. | |
| 2003/0208122 A1 | 11/2003 | Melkent et al. | |
| 2004/0059260 A1 | 3/2004 | Truwit | |
| 2004/0176750 A1 | 9/2004 | Nelson et al. | |
| 2004/0243147 A1 | 12/2004 | Lipow | |
| 2004/0255991 A1 | 12/2004 | Truwit et al. | |
| 2004/0260323 A1 | 12/2004 | Truwit et al. | |
| 2004/0267284 A1 | 12/2004 | Parmer et al. | |
| 2006/0192319 A1 | 8/2006 | Solar | |
| 2006/0195119 A1 | 8/2006 | Mazzocchi et al. | |
| 2007/0250078 A1 | 10/2007 | Stuart | |
| 2007/0299427 A1 | 12/2007 | Yeung et al. | |
| 2008/0004632 A1 | 1/2008 | Sutherland et al. | |

FOREIGN PATENT DOCUMENTS

| | | |
|---|---|---|
| DE | 3937052 | 5/1990 |
| DE | 29612100 | 9/1996 |

| | | |
|---|---|---|
| DE | 19726141 | 1/1999 |
| DE | 19826078 | 8/1999 |
| DE | 19808220 | 9/1999 |
| DE | 19820808 | 11/1999 |
| EP | 0386936 | 5/1990 |
| EP | 0427358 | 5/1991 |
| EP | 0609085 | 8/1994 |
| EP | 0724865 | 8/1996 |
| EP | 0832611 | 4/1998 |
| EP | 0904741 | 3/1999 |
| GB | 2237993 | 5/1991 |
| GB | 2329473 | 3/1999 |
| GB | 2346573 | 8/2000 |
| WO | WO-8809151 | 12/1988 |
| WO | WO-9522297 | 8/1995 |
| WO | WO-9610368 | 4/1996 |
| WO | WO-9633766 | 10/1996 |
| WO | WO-9703609 | 2/1997 |
| WO | WO-9721380 | 6/1997 |
| WO | WO-9742870 | 11/1997 |
| WO | WO-9817191 | 4/1998 |
| WO | WO-9825535 | 6/1998 |
| WO | WO-9851229 | 11/1998 |
| WO | WO-0001316 | 1/2000 |
| WO | WO-0018306 | 4/2000 |
| WO | WO-0124709 | 4/2001 |
| WO | WO-0149197 | 7/2001 |
| WO | WO-0176498 | 10/2001 |
| WO | WO-2004026161 A2 | 4/2004 |

OTHER PUBLICATIONS

Ritter, R., et al., "Stereotaxie Magnetique: Deplacement D'Implants dans le Cerveau, Assistes par Ordinateur et Guides par Imagerie", Innovation et Technologie en Biologie et Medecine, 13, (1992), 437-449.

"Fathom Remote Introducer", *Image-Guided Neurologics, Inc.*, CNS Hynes Convention Center, (Oct. 30-Nov. 4, 1999), 2 pgs.

"Inomed Competence in Neurophysiologic Monitoring", http://www.inomed.com/english/index.htm, (observed Mar. 23, 2004), 2 pgs.

"MicroTargeting® Precision Guidance Using Microelectrode Recording", (Aug. 15, 2003), 5 pgs.

"Possible Existence of Common Internalization Mechanisms among Arginine-rich Peptides", Suzuki, T. et al., Journal of Biological Chemistry, vol. 277, No. 4 (2002) pp. 2437-2443.

Allison, S., et al., "Microchannel Plate Intensifier Response in Traverse Magnetic Field", Electronic Letters, 26, (Jun. 7, 1990), 770-771.

Drake, J. M., et al., "ISG Viewing Wand System", *Neurosurgery*, 34 (6), (Jun. 1994).

Dyer, P. V., et al., "The ISG Viewing Wand: an application to atlanto-axial cervical surgery using the Le Fort I maxillary osteotomy", *British Journal of Oral and Maxillofacial Surgery*, 33, (1995), pp. 370-374.

Franck, Joel, et al., "microTargeting® Platform System incorporating StarFix™ guidance", *microTargeting*, (2001-2002), p. 44.

Gehring, W. J., "Homedomain Proteins", Annu. Rev. Biochem., vol. 63 (1997) pp. 487-526.

Gillies, G., et al., "Magnetic Manipulation Instrumentation for Medical Physics Research", Review of Scientific Instruments, 65 (3), Review Article, (Mar. 1994), 533-562.

Grady, M. S., "Magnetic Stereotaxis System for Neurosurgical Procedures", *Proceedings of the 37th International Instrumentation Symposium*, (May 5-9, 1991), pp. 665-675.

Grady, M. S., et al., "Initial Experimental Results of a New Stereotaxic Hyperthermia System", *American College of Surgeons, Surgical Forum, vol. XXXIX, Neurological Surgery*, (1988), pp. 507-509.

Grady, M. S., et al., "Magnetic Stereotaxis: A Technique to Deliver Stereotactic Hyperthermia", *Neurosurgery*, 27 (6), (1990), pp. 1010-1016.

Grady, M. S., et al., "Preliminary experimental investigation of in vivo magnetic manipulation: Results and potential application in hyperthermia", *Medical Physics*, 16 (2), (Mar./Apr. 1989), pp. 263-272.

Grady, M., et al., "Nonlinear Magnetic Stereotaxis: Three-Dimensional, in vivo Remote Magnetic Manipulation of a Small Object in Canine Brain", *Medical Physics*, 17 (3), (May/Jun. 1990), pp. 405-415.

Hata, N., et al., "Needle Insertion Manipulator for CT- and MR-Guided Stereotactic Neurosurgery", *Interventional MR: Techniques and Clinical Experience*, St. Louis : London : Mosby ; Martin Dunitz, F. Jolesz and I. Young, eds., (1998), pp. 99-106.

Hirschberg, H., et al., "Image-guided neurosurgery—MR compatible stereotactic equipment", http://www.medinnova.no/English/P51466ster.html, (Mar. 29, 2001), 1 pg. (viewed website on Mar. 29, 2001).

Hirschberg, Henry, et al., "Image-guided neurosurgery", stereotactic equipment for MR imaging, http://www.medinnova.no/English/P51466ster.html, (Observed Mar. 8, 2002), 1 page.

Howard III, M. A., et al., "Magnetic Neurosurgery: Image-Guided Remote-Controlled Movement of Neurosurgical Implants", *Clinical Neurosurgery*, (1995), pp. 382-391.

Howard III, M. A., et al., "Review of Magnetic Neurosurgery Research", *Journal of Image Guided Surgery*, 1 (6), (1995), pp. 295-299.

Howard, M. A., et al., "Magnetic Movement of a Brain Thermoceptor", *Neurosurgery*, 24 (3), (Mar. 1989), pp. 444-448.

Howard, M. A., et al., "Magnetic Neurosurgery", Proceedings of the Meeting of the American Society for Stereotactic and Functional Neurosurgery, (Mar. 8-11, 1995), pp. 102-107.

Lawson, M. A., et al., "Near Real-Time Bi-planar Fluoroscopic Tracking System for the Video Tumor Fighter", Spie, vol. 1445 Image Processing, (1991), pp. 265-275.

Leggett, W.B., et al., "Surgical Technology—The Viewing Wand: A New System for Three-Dimensional Computed Tomography-Correlated Intraoperative Localization", *Current Surgery*, (Dec. 1991), pp. 674-678.

Malison, R. T., et al., "Computer-Assisted Coregistration of Multislice SPECT and MR Brain Images by Fixed External Fiducials", Journal of Computer Assisted Tomography, 17 (6) (1993) pp. 952-960.

Mannervik, M., "Target genes of homeodomain proteins", BioEssays vol. 21.4 (Apr. 1999) pp. 267-270.

McNeil, R. G., et al., "Characteristics of an Improved Magnetic-Implant Guidance System", *IEEE Transactions on Biomedical Engineering*, 42 (8), (Aug. 1995), pp. 802-808.

Meeker, D., et al., "Optimal Realization of Arbitrary Forces in a Magnetic Stereotaxis System," IEEE Transactions on Magnetics, 32 (2), (Mar. 1996), 320-328.

Molloy, J. A., et al., "Experimental Determination of the Force Required for Insertion of a Thermoseed Into Deep Brain Tissues", *Annals of Biomedical Engineering*, 18 (3) (1990), pp. 299-313.

Molloy, J. A., et al., "Thermodynamics of movable inductively heated seeds for the treatment of brain tumors", *Medical Physics*, 18 (4) (Jul./Aug. 1991), pp. 794-803.

Oliver, L., "Cup-And-Ball Chemopallidectomy Apparatus", (1958), p. 410.

Patikoglou, G. et al., "Eukaryotic Transcription Factor-DNA Complexes", Annual Review of Biophysics and Biomolecular Structure vol. 26 (1997) pp. 289-325.

Quate, E., et al., "Goniometric Motion Controller for the Superconducting Coil in a Magnetic Stereotaxis System", IEEE Transactions on Biomedical Engineering, 38 (9), (Sep. 1991), 899-905.

Ramos, P. A., et al., "Electro-optic imaging chain for a biplanar fluoroscope for neurosurgery: magnetic field sensitivity and contrast measurements", *Optical Engineering*, 32 (7) (Jul. 1993), pp. 1644-1656.

Ramos, P. A., et al., "Low-dose, magnetic field-immune, bi-planar fluoroscopy for neurosurgery", *SPIE Medical Imaging V: Image Physics*, vol. 1443, (1991), pp. 160-170.

Ramos, P. A., et al., "Microchannel Plate Image Intensifier Electron Dynamics in Magnetic Field", *Electronics Letters*, 27 (18), (Aug. 29, 1991), pp. 1636-1638.

Ritter, R. C., et al., "Magnetic Stereotaxis: An Application of Magnetic Control Technology to the Needs of Clinical Medicine", *Proc. of the MAG'95 Industrial Conf. and Exhibition, Technomic Pub. Co.*, Lancaster PA, Allaire, P., ed., (1995), pp. 186-193.

Ritter, R. C., et al., "Magnetic Stereotaxis: Computer-Assisted Image-Guided Remote Movement of Implants in the Brain", *Computer-Integrated Surgery: Technology and Clinical Applications*, MIT Press, (1996), pp. 363-369.

Sandeman, D. S., et al., "Advances in image-directed neurosurgery: Preliminary experience with the ISG Viewing Wand compared with the Leksell G frame" *British Journal of Neurosurgery*, 8(1994), pp. 529-544.

Stein, S. et al., "Checklist: Vertebrate homeobox genes", Mechanisms of Development, vol. 55, No. 1 (Mar. 1996) pp. 91-108.

Szikora, I., et al., "Endovascular Treatment of Experimental Aneurysms with Liquid Polymers: The Protective Potential of Stents", *Neurosurgery*, 38, (Feb. 1996), pp. 339- 347.

Vollmer, J. et al., "Homeobox Genes in the Developing Mouse Brain", Journal of Neurochemistry, vol. 71, No. 1 (Jul. 1998) pp. 1-19.

Wolberger, C., "Homeodomain Interactions", Current Opinion in Structural Biology vol. 6, No. 1 (Feb. 1996) pp. 62-68.

Yeh, H.-S., et al., "Implantation of intracerebral depth electrodes for monitoring seizures usign the Pelorus stereotactic system guided by magnetic resonance imaging", *J. Neurosurg.*, 78(1993), pp. 138-141.

Zinreich, S. J., et al., "Frameless Stereotaxic Integration of CT Imaging Data: Accuracy and Initial Applications", *Radiology*, 188 (3), (1993), pp. 735-742.

Supplementary European Search Report mailed Oct. 26, 2009 for EP05852969 filed Dec. 6, 2005 claiming benefit of U.S. Appl. 11/005,907, filed Dec. 5, 2004.

\* cited by examiner

MULTI-LUMEN INSTRUMENT GUIDE

RELATED APPLICATIONS

This application is related to U.S. patent application Ser. No. 11/005,607, filed on Dec. 4, 2004, entitled "INSTRUMENT GUIDING STAGE APPARATUS AND METHOD FOR USING SAME," the disclosure of which is incorporated herein by reference in its entirety.

This application is related to U.S. patent application Ser. No. 10/370,090, filed on Feb. 20, 2003, entitled "TRAJECTORY GUIDE WITH ANGLED OR PATTERNED GUIDE LUMENS OR HEIGHT ADJUSTMENT," the disclosure of which is incorporated herein by reference in its entirety.

TECHNICAL FIELD

This document relates generally to guiding instruments and in particular, but not by way of limitation, to a multi-lumen insert, such as for use with a trajectory guide for surgically guiding instruments.

BACKGROUND

Neurosurgery sometimes involves inserting an instrument through a burr hole or other entry portal into a subject's brain toward a target region of the brain. Because of the precision needed to reach the target, while avoiding nearby structures that are often critical to brain function, precise guidance devices and techniques are needed. In one such technique a multi-lumen instrument guide is included within a trajectory guide mounted to the skull. An instrument is inserted through a guide lumen of the instrument guide, which steers it toward the target.

DETAILED DESCRIPTION

Figure 1:
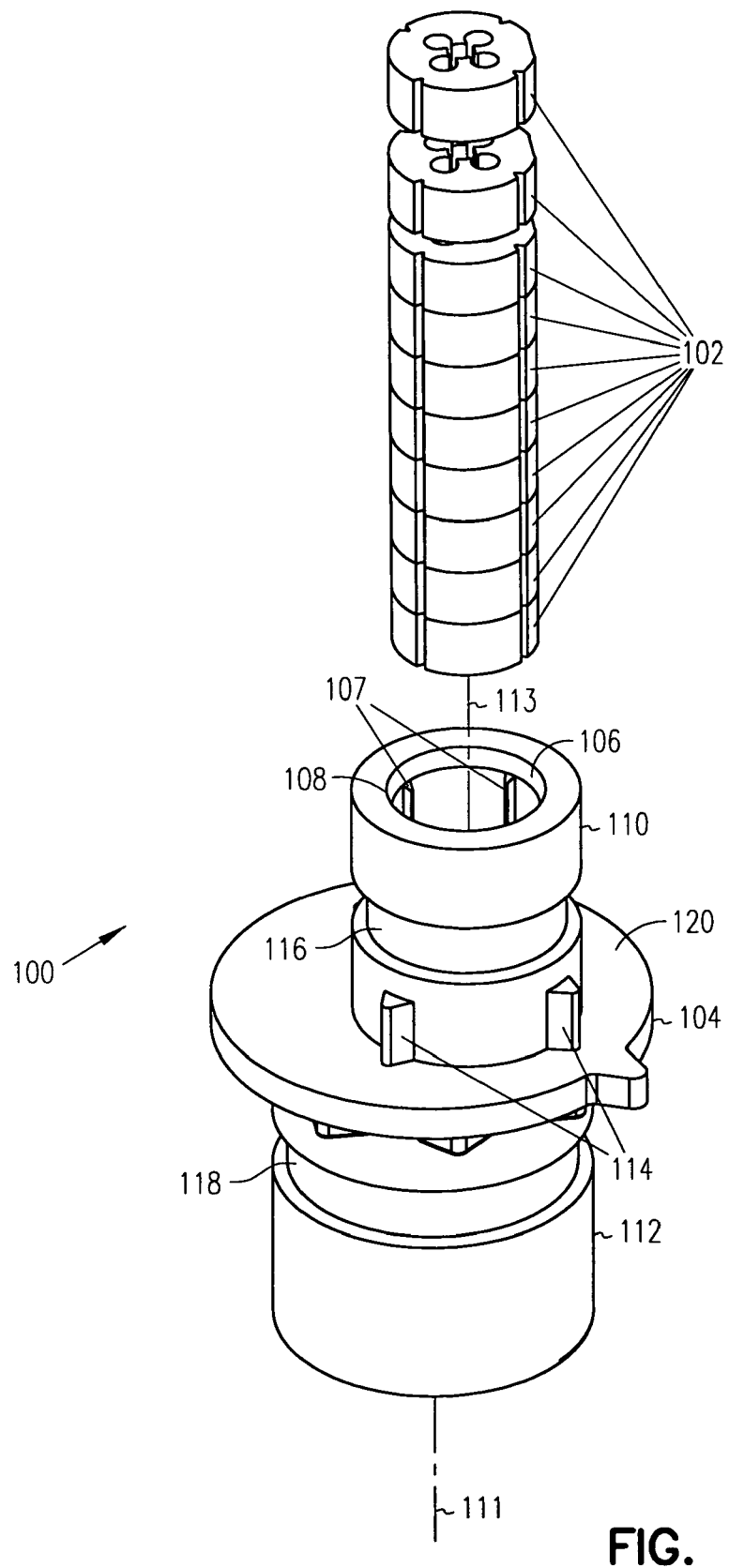
FIG. 1 is an exploded view illustrating guide layers and a guide coupler.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated references(s) should be considered supplementary to that of this document; for irreconcilable inconsistencies, the usage in this document controls.

In order to accurately plunge an instrument into the brain, the instrument typically must be aligned to and guided on the proper trajectory toward the target. The better an instrument is aligned to and held on the ideal trajectory, the more accurate will be the guidance and placement of the instrument at the target.

Many surgical instruments are long, thin, slightly flexible tubes or rods. Guiding such an instrument, therefore, typically involves guiding a round tube in a round guide hole (also referred to as a guide lumen) as the tube passes through the hole (and beyond, toward the target). The guided instrument should remain as nearly concentric to and as nearly parallel to the guide lumen as possible. This concentricity and parallelism should extend even at relatively long distances from the exit of the guide lumen. Stated another way, the instrument's concentricity and parallelism to the ideal trajectory should be adequate at a specified target distance from the guiding apparatus.

Among the characteristics that will improve tubular instrument guidance are: (1) a tighter fit between an inner diameter of the guide lumen and an outer diameter of the tubular instrument; (2) a longer axial engagement or guidance of the tubular instrument with the guide lumen (i.e., a long-bore in the guide lumen); (3) a shorter distance from the guide lumen exit to the target (i.e., placing the guiding apparatus closer to the brain or other target); and/or (4) a stiffer instrument being guided toward the target.

However, manufacturing long, small-bore holes, such as needed for instrument guidance, can be difficult and costly, particularly where a pattern of multiple small-bore holes is required, instead of a single small-bore hole, and even more particularly where the multiple small-bore holes must be closely spaced to each other. Small-bore holes are typically made by techniques including: drilling (such as normal machining, laser drilling, electrical discharge machining (EDM), or the like); molding material around a pin, then removing the pin; or extruding a tube with an inside diameter equal to that of the desired small-bore hole.

Drilled holes often have a practical limit on the obtainable depth. An adequately long, straight, drilled hole suitable for accurate instrument guidance is often difficult or impossible to obtain. Although exotic methods such as laser drilling or EDM may work, their costs are typically high and the materials with which they may be used are typically limited. Even if a single long small-bore hole can be drilled, for example, drilling another nearby hole can be very difficult because the drill bit may wander or break through the material separating the adjacent small-bore holes.

Molding long holes is possible. However, molding draft (i.e., taper) is usually required, especially for long holes. Even with such molding draft, as a practical matter, molded small-bore holes are limited to a modest length. The pins that form such holes are typically too weak and flexible when they are made too long. Moreover, drafted holes will affect the tightness of fit between the instrument and the hole, making it difficult for a drafted molded hole to provide adequate instrument guidance.

An extruded tube may alternatively be inserted as a liner in a larger diameter hole to more snugly guide the tubular instrument. Alternatively, the wider end of the tapered small-bore hole could be plugged with a sleeve to narrow its effective inner diameter. However, each of these techniques proves difficult when multiple closely-spaced small-bore holes are needed. The material separating the closely-spaced holes becomes too thin and frangible.

Another technique would be to align two shorter, separated multi-lumen guides. However, aligning the guides to each other is difficult, and the user must spear the instrument through a guide lumen not only at the proximal guide, but at the distal guide as well. This can be awkward for the user, and it is possible that the instrument could enter the wrong guide lumen in the more distal guide, thereby deflecting along the wrong trajectory into the brain and away from the desired target.

Drilling, molding, extrusion, and other techniques, therefore, all present problems when multiple closely-spaced small-bore holes are needed. Opting for a shorter bore instrument guide, however, will compromise the accuracy with which the instrument can be guided toward the target.

Among other things, the present inventors have recognized difficulties with ordinary manufacturing techniques to construct multi-lumen instrument guides with tight tolerance passages to provide accurate targeting of instruments. The present inventors have also recognized an unmet need for reducing trauma to the brain through enhanced flexibility in instrument targeting where the center to center distance of passages within multi-lumen instrument guides is reduced (i.e., instruments are able to accurately traverse around blood vessels, vital tissues, and the like).

FIG. 1 is an exploded perspective view of an example of an instrument guide 100. The instrument guide 100 includes at least two guide layers 102. In the example shown in FIG. 1, the instrument guide 100 includes ten guide layers 102. Optionally, the instrument guide 100 includes additional guide layer 102 or fewer guide layers 102. In one example, the instrument guide 100 includes a guide coupler 104 carrying the guide layers 102. In one example, the inner surface 106 of the guide coupler 104 defines a guide layer lumen 108. The guide layer lumen 108 is cylindrical in one example. In another example, the guide layer lumen 108 has a different geometry, for example a rectangle, triangle, oval or the like. Optionally, the inner surface 106 is sized and shaped to snugly retain the guide layers 102. In another example, one or more ridges 107 extend from the inner surface 106 into the guide layer lumen 108. In one example, the ridges 107 are disposed along the inner surface 106 approximately every 90 degrees. In another example, the ridges 107 are disposed at lesser or greater increments. Optionally, the ridges 107 have a triangular cross-sectional geometry. In an example, the base of a ridge 107 extends from the inner surface 106 to an edge within the guide layer lumen 108.

In an example, the guide coupler 104 includes an upper portion 110 and a lower portion 112. In one example, the upper portion 110 has a smaller outer perimeter than the lower portion 112. In other words, the upper portion 110 is narrower than the lower portion 112. In the example of FIG. 1, the upper portion 110 is parallel to a longitudinal center axis 111 of the guide coupler 104 and offset from the longitudinal center axis 111. In other words, the longitudinal center axis 113 of the upper portion 110 is offset from the longitudinal center axis 111 of the guide coupler 104. In another example, the upper portion 110 longitudinal center axis 113 is aligned with the longitudinal center axis 111 of the guide coupler 104.

The guide coupler upper portion 110 optionally includes keys 114 disposed around the outer perimeter of the upper portion 110. In one example, the keys 114 are disposed around an outer perimeter of the upper portion 110 at 90 degree increments. The outer perimeter of the upper portion 110, in an example, includes a first recess 116. In the example shown in FIG. 1, the first recess 116 extends circumferentially around the upper portion 110. In another example, the first recess 116 extends part way around the upper portion 110. In yet another example, a second recess 118 extends around the lower portion 112. Optionally, the second recess 118 extends part way around the lower portion 112. A flange 120 is interposed between the upper portion 110 and lower portion 112. In an example, the flange 120 has an outer perimeter greater than that of the upper portion 110 and lower portion 112. In another example, the flange 120 extends part way around the guide coupler 104.

In one example, the guide coupler 104 and guide layer 102 are constructed with hardenable materials such as, but not limited to, polycarbonate, injection molded plastics, epoxies and the like. In another example, the guide coupler 104 and guide layer 102 are made, at least partially, with a thermoplastic having polyamide with the trade name Grilamid®, which is registered to EMS-Grivory. In still another example, the guide coupler 104 and guide layer 102 are made with any biocompatible material. Optionally, the guide coupler 104 and guide layer 102 are constructed with differing materials.

Figure 2:
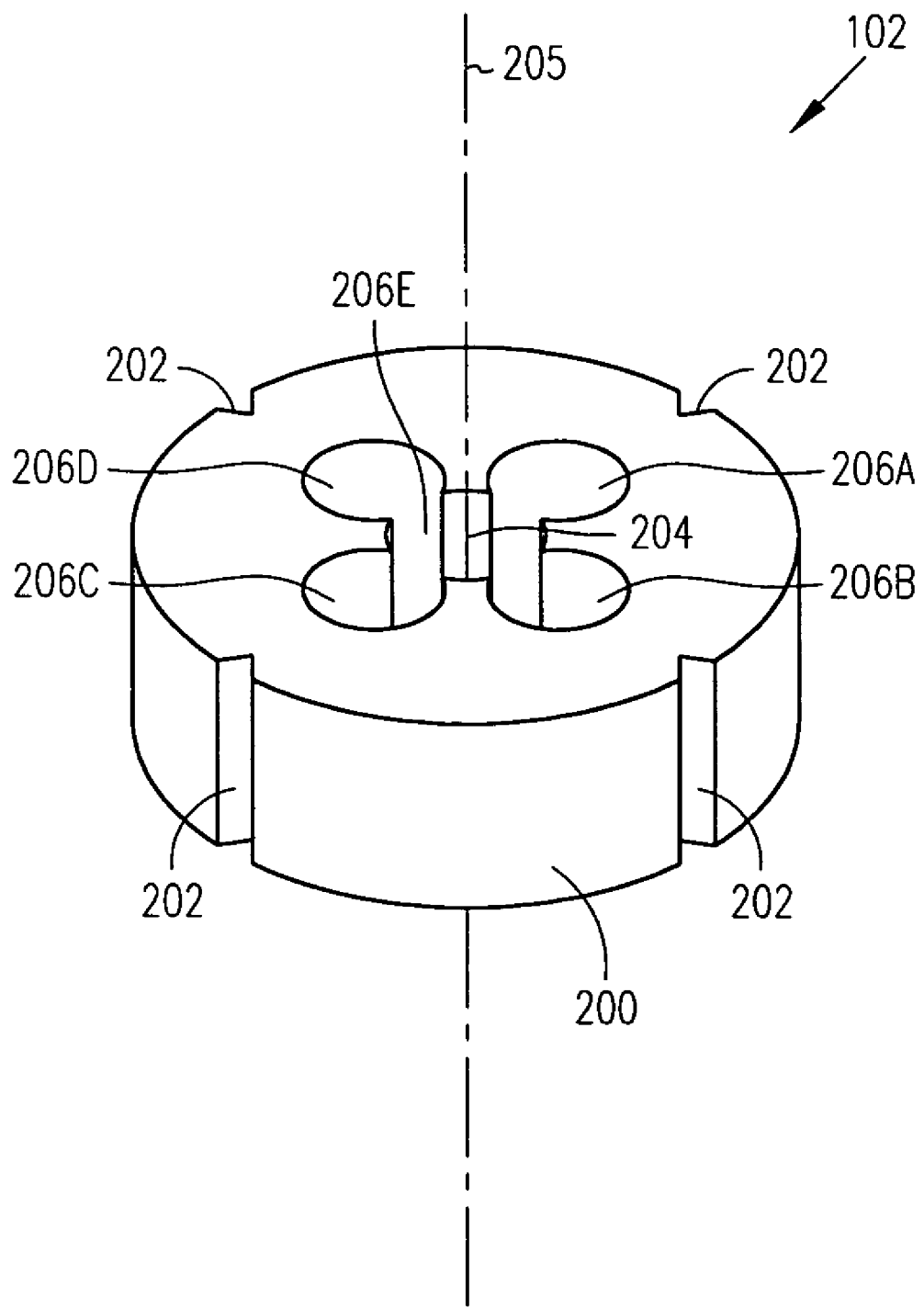
FIG. 2 is a perspective view illustrating a first guide layer.

FIG. 2 is a perspective view of a guide layer 102. In one example, the outer perimeter 200 of the guide layer 102 has a substantially cylindrical geometry and the guide layer 102 has a diameter of approximately 0.4 inches. In another example, the outer perimeter 200 has a different geometry, for example rectangular, triangular, ovular or the like. In an example, the outer perimeter 200 is sized and shaped to snugly fit within the inner surface 106 of the guide coupler 104. In an example, the guide layer 102 includes grooves 202 disposed around the outer perimeter 200. In the example shown in FIG. 2, four grooves 202 are disposed around the guide layer 102. Optionally, fewer or additional grooves 202 are disposed around the guide layer 102. In one example, the grooves 200 extend from an upper surface of the guide layer 102 to a lower surface. In another example, the grooves 202 are disposed around the guide layer 102 at approximately 90 degree increments. In yet another example, the grooves 202 are disposed at differing increments. In one option, the grooves 202 have a corresponding geometry to ridges 107. In an example, the grooves have a triangular geometry. In another example, the ridges 107 are sized and shaped to snugly fit within the grooves 202. The ridges 107 and grooves 202 cooperatively align different stacked guide layers 102 with the guide coupler 104, and with each other, when the guide layers 102 are disposed within the guide layer lumen 108. In still another example, ridges extend from the guide layers 102 into grooves disposed on the inner surface 106 of the guide coupler 104. Optionally, the guide layers and the guide coupler have non-circular geometries (e.g., triangular, ovular, and the like) that facilitate alignment without the ridges and grooves.

The guide layer 102 optionally further includes at least one substantially untapered instrument passage 204. The instrument passage 204 extends through the guide layer 102 and is non-threaded. In another example, the instrument passage 204 is a channel disposed on the guide layer 102. In yet another example, the instrument passage 204 is a lumen disposed within the guide layer 102. The longitudinal center axis 205 of the instrument passage 204, is optionally coincident with the longitudinal center axis of the guide layer 102. In another example, the longitudinal center axis 205 of the instrument passage 204 is parallel to but offset from the longitudinal center axis 205 of the guide layer 102. In still another example, the instrument passage 204 longitudinal center axis 205 is not parallel with the longitudinal center axis of the guide layer 102. In other words the instrument passage 204 is at an angle to the longitudinal center axis of the guide layer 102. The instrument passage 204 has an inner diameter that is circular, elliptical, rounded, chamfered or the like, in one example.

In the example shown in FIG. 2, the instrument passage 204 includes five substantially untapered channels 206A-E. In other words, the diameter of the approximately cylindrical channels 206A-E remains substantially unchanged throughout the guide layer 102, and throughout the middle additional stacked guide layers 102. The substantially untapered characteristic of the channels 206A-E ensures there is a tight clearance between instruments and the guide layers 102. The substantially untapered channels 206A-E, in one example, include a slight taper so at least a portion of the inner diameter of the channels 206A-E provides a tight tolerance slidable coupling with an instrument. In an example, the channels 206A-E are interconnected, as shown in FIG. 2. A common inner surface of instrument passage 204 defines the channels 206A-E. In another example, channels 206A-E are separate and distinct cylindrical lumens rather than being interconnected. In an example, the channels 206A-D are disposed around substantially centered channel 206E, such as at 90 degree increments approximately. This can be conceptualized as a North-South-East-West configuration about the centered channel 206E. Optionally, some or all of channels 206A-E are not interconnected. In one example, additional channels are provided in guide layer 102. In still another example, the channels are disposed within guide layer 102 in a different pattern, for example a three by three matrix of channels, or the like. In yet another example, the instrument passage includes two or more channels disposed in a pattern. Referring again to the example shown in FIG. 2, each of the channels 206A-E, optionally have a diameter of about 0.075 inches and are spaced from the other adjacent channels 206A-E about 0.0787 inches center-to-center.

In the example of FIG. 1, the instrument guide 100 includes multiple guide layers 102 stacked within guide coupler 104. The guide layers 102 are disposed within guide layer lumen 108, such as with the ridges of the guide coupler 104 disposed within grooves 202 of the guide layers 102. This retains the individual guide layers 102 within the guide layer lumen 108 in a desired orientation. In other words, the ridges 107 and corresponding grooves 202 align the instrument passage 204 of one guide layer 102 with the instrument passages 204 of the other guide layers 102 disposed within the guide layer lumen 108. Further, the channels 206A-E of one guide layer 102 are also aligned with the channels 206A-E of the other guide layers 102 through the cooperative relationship of the ridges 107 and grooves 202. The channels 206A-E thus define substantially untapered passages extending through the stacked guide layers 102. In other words, the channels 206A-E are sized and shaped to create tight tolerance passages that accurately maintain a consistent diameter through the entire stack of guide layers 102. This ensures accurate tracking of instruments snugly coupled to the guide layers 102 within channels 206A-E and fed through the instrument guide 100.

The substantially untapered channels 206A-E of the guide layers 102, shown in FIG. 1, are symmetrical in the example described above. As a result, the guide layers 102 can be assembled in any orientation in which they will fit into the guide layer lumen 108 (e.g. by disposing the ridges 10 within the grooves 202) and define the substantially untapered passages extending through the stacked guide layers 102. The guide layers 102, in one example, are substantially identical and interchangeable. Interchangeable guide layers 102 expedite assembly of the instrument guide 100 as the guide layers are stacked in any order or orientation (for instance, top side down or bottom side up) within the guide coupler 104.

In another example, the guide layers 102 include channels 206A-E that have a slight taper (described above). When the guide layers 102 are stacked in the guide coupler 104 the channels 206A-E provide substantially untapered passages. The effect of the greater clearance between the channels 206A-E and an instrument caused by the slight taper is lessened as at least a portion of the inner diameters of the channels 206A-E provides a tight tolerance slidable coupling to instruments. Coupling the guide layers 102 together further overcomes the effect of the slight taper as each elongated passage includes multiple tight tolerance inner diameter portions that slidably couple with the instruments. As a result, channels 206A-E provide substantially untapered passages when the guide layers 102 are stacked.

Figure 3:
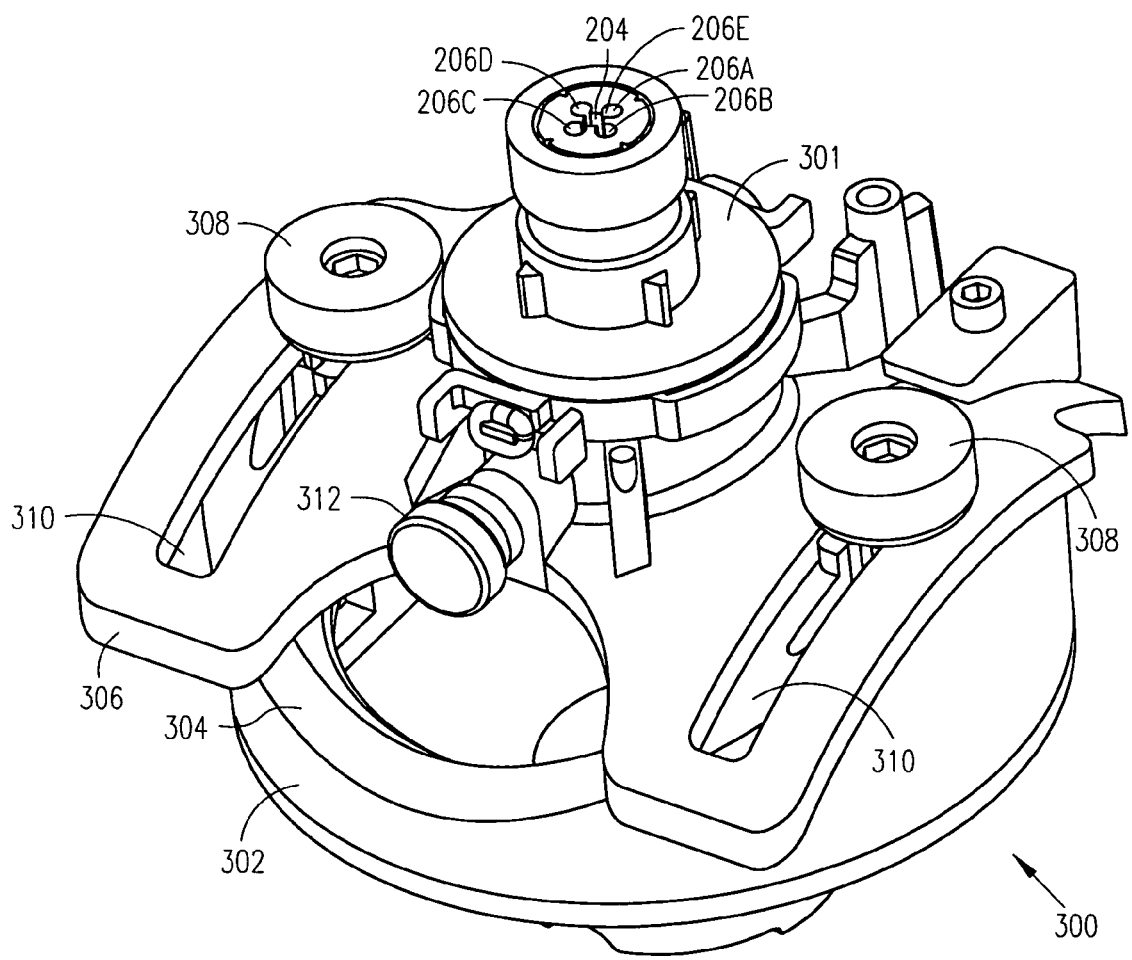
FIG. 3 is a perspective view illustrating a centered instrument guide coupled to a trajectory alignment assembly.

FIG. 3 shows a perspective view of an instrument guide 301 coupled to a trajectory alignment assembly 300. The instrument guide 301 of FIG. 3 is similar to the instrument guide 100. However, the instrument guide 301 includes an instrument passage 204 with a centered channel 206E that is substantially coincident with a longitudinal axis of the instrument guide 301. Trajectory alignment assembly 300 includes a base ring 302. In one example, the base ring 302 is coupled to an instrument immobilizer or other fixture that is disposed around a burr hole in a patient's skull. In another example, the base ring 302 is coupled to the skull or another portion of the body. A rotatable base 304 is coupled to the base ring 302 and operable to rotate around the base ring 302. A saddle slide 306 is disposed on an arcuate top portion of the rotatable base 304. In an example, the saddle slide 306 is slidably coupled to the rotatable base 304. In one example, fasteners 308, such as thumbscrews or the like, extend through the saddle slide 306 and the rotatable base 304. The fasteners 308 are disposed within slots 310 in the saddle slide 306. In an example, the saddle slide 306 is slidable over the rotatable base 304 when the fasteners 308 are loosened. The saddle slide 306 includes an instrument guide lumen carrying the instrument guide 301.

As described above, the lower portion 110 of the guide coupler 104 includes the recess 118. In an example, thumbscrew 312 extends through the wall of saddle slide 306 that defines the instrument guide lumen. When tightened, the thumbscrew 312 engages against the surface defining the recess 118 to securely retain the instrument guide 100 within the instrument guide lumen. Thus, the recess 118 assists in preventing the instrument guide from moving into or out of the instrument guide lumen when the thumbscrew 312 is secured. In another example, the guide coupler 104 includes keys extending from the lower portion 110. These keys are sized and shaped to fit within corresponding grooves in the trajectory alignment assembly. The relation of the keys to the grooves of the trajectory alignment assembly 300 substantially prevents unwanted relative rotation between the instrument guide 100 and the trajectory alignment system 300.

In another example, the trajectory alignment assembly 300 is then rotationally and arcuately moveable to orient the channels 206A-E of instrument guide 100 along a desired track through the burr hole and into the skull. In other words, the trajectories defined by channels 206A-E are positionable arcuately and rotationally to extend through the burr hole and into the skull. One example of the trajectory alignment assembly 300 is further described in U.S. patent application Ser. No. 10/671,913, filed on Sep. 25, 2003, which is assigned to the assignee of the present application and which is incorporated by reference herein in its entirety. Additional examples of trajectory guide assemblies are shown in U.S. patent application Ser. No. 09/828,451, filed on Apr. 6, 2001, which is assigned to the assignee of the present patent application, and which is incorporated by reference herein in its entirety.

Figure 4:
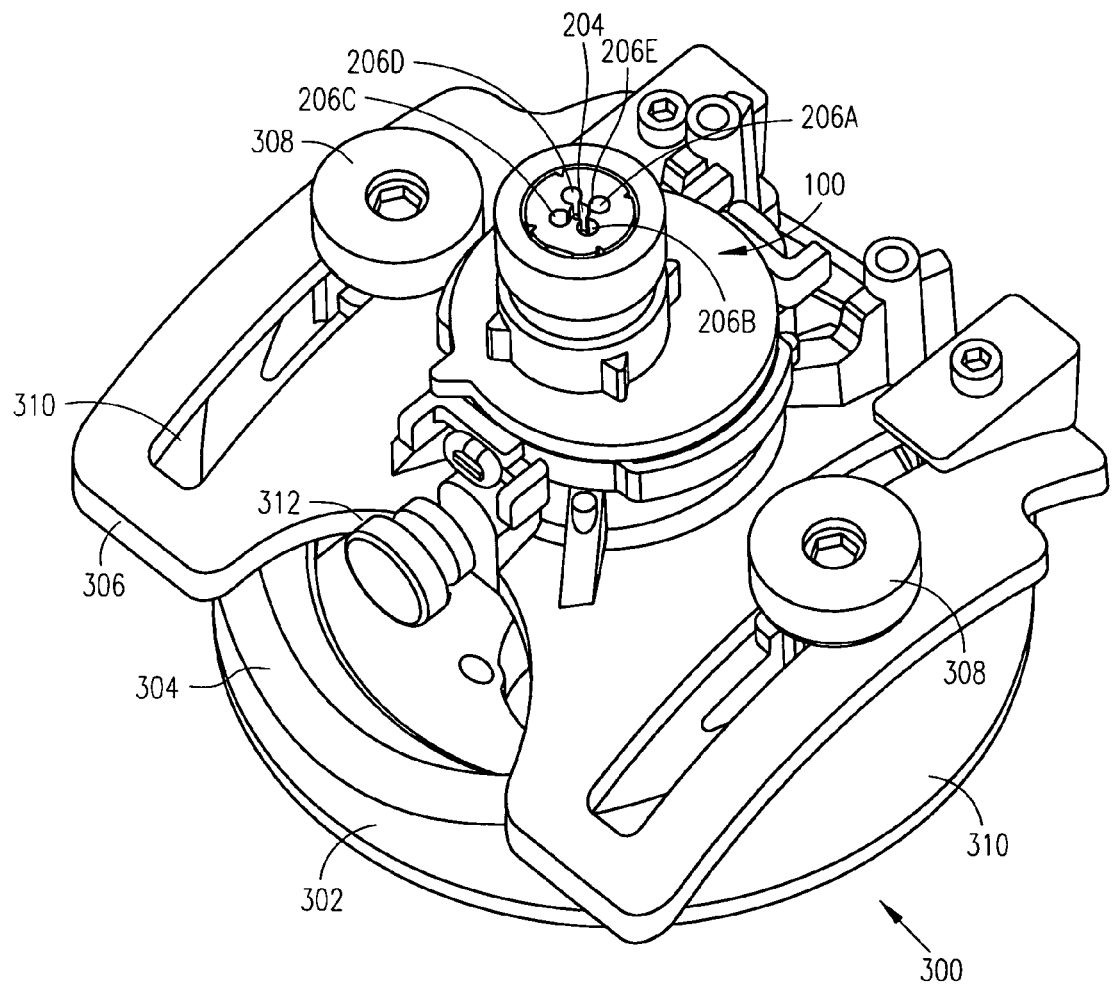
FIG. 4 is a perspective view illustrating an offset instrument guide coupled to a trajectory alignment assembly.

FIG. 4 is a perspective view of the instrument guide 100 coupled to the trajectory alignment assembly 300. The instrument guide 100 of FIGS. 1 and 4 is similar to the instrument guide 301, described above. However, the instrument guide 100 includes an instrument passage 204 with an offset channel 206E that is substantially parallel to a longitudinal axis of the instrument guide 100, but offset therefrom.

Figure 5:
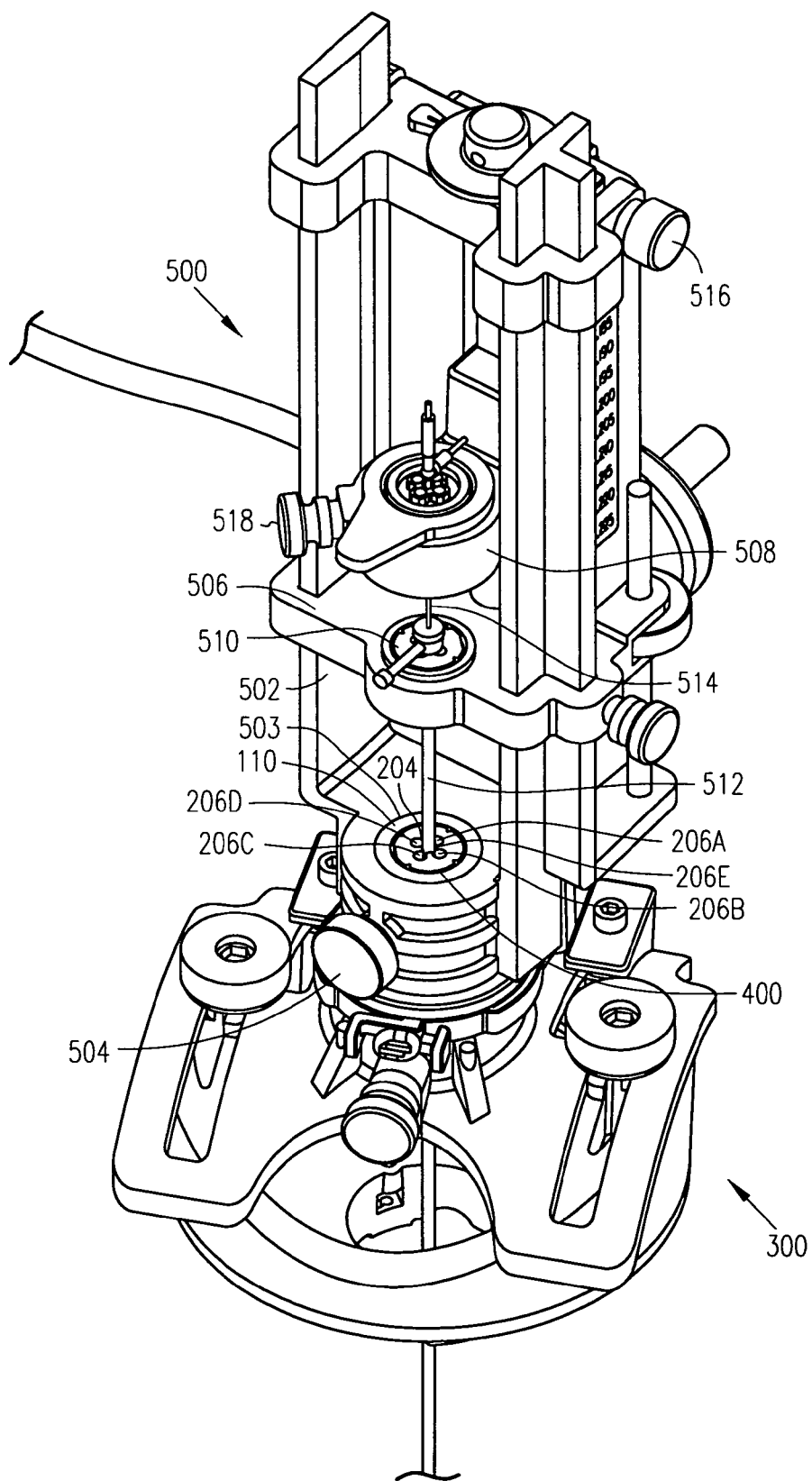
FIG. 5 is a perspective view illustrating an instrument guide coupled to a trajectory alignment assembly and a translating stage with an instrument extending through the instrument guide.

FIG. 5 is a perspective view of an instrument guide 400 coupled to a trajectory alignment assembly 300 and a translating stage 500, which is also sometimes referred to as a microdrive introducer. The translating stage 500 includes a base 502. In an example, the base 502 includes an orifice 503 within which the upper portion 110 of the instrument guide 400 is located. The upper portion 110 includes the recess 116. A thumbscrew 504, or other fastener, is tightened and engages the surface defining the recess 116 to retain the translating stage 500 around the instrument guide 400. In an example, the instrument guide 400 is adapted to couple with the translating stage 500. In one example, a first stage 506 is moveably coupled to the base 502. In another example, the first stage 506 is translatable toward or away from the instrument guide 400. The first stage 506 moves in directions substantially parallel to the channels 206A-E in instrument guide 400. A second stage 508 is moveably coupled to the first stage 506. In an example, the second stage 508 is independently translatable toward or away from the instrument guide 400.

In the example of FIG. 5, the first stage 506 includes a stop 510 for a guide tube 512. In another example, the guide tube 512 includes a flange that engages the stop 510. The guide tube 512 is plunged through one of the channels 206A-E of the instrument guide 400. In an example, the instrument guide channels 206A-E are sized and shaped to snugly pass the outer perimeter of the guide tube 512. This provides an accurate track to a desired target for the guide tube 512. In another example, a different instrument 514 is retained in a retaining assembly 516 coupled to the second stage 508. In one example, tightening of the thumbscrew 518 retains the instrument 514. In another example, the instrument 514 is plunged through the guide tube 512 toward a target. The guide tube 512 is sized and shaped to snugly pass the outer perimeter of the instrument 514. The coupling of the guide layer 102 to the guide tube 512 and the coupling of the guide tube 512 to the instrument 514 provides an accurate track to the target. The trajectory defined by the substantially untapered channel 206E, in this example, is translated to the instrument 514 and guide tube 512 to provide precise tracking to a desired target. The substantially untapered inner surface of the channels 206A-E provides snug coupling between the guide layer 102 and the guide tube 512 so the guide tube 512 and instrument 514 mirror the trajectory of the channels 206A-E.

In another example, additional tubes are disposed between the inner surface of the guide tube 512 and the instrument 514. In one example, the instrument 514 has a smaller diameter, and a spacer tube is provided to snugly couple between the instrument 514 and the guide tube 512. In still another example, the instrument 514 is a stimulation or sensing electrode, catheter, or the like. Additional examples of translatable stages, guide tubes, and instruments are shown in U.S. application Ser. No. 11/005,607 filed on Dec. 4, 2004, which is assigned to the assignee of the present patent application, and which is incorporated by reference herein in its entirety.

Figure 6:
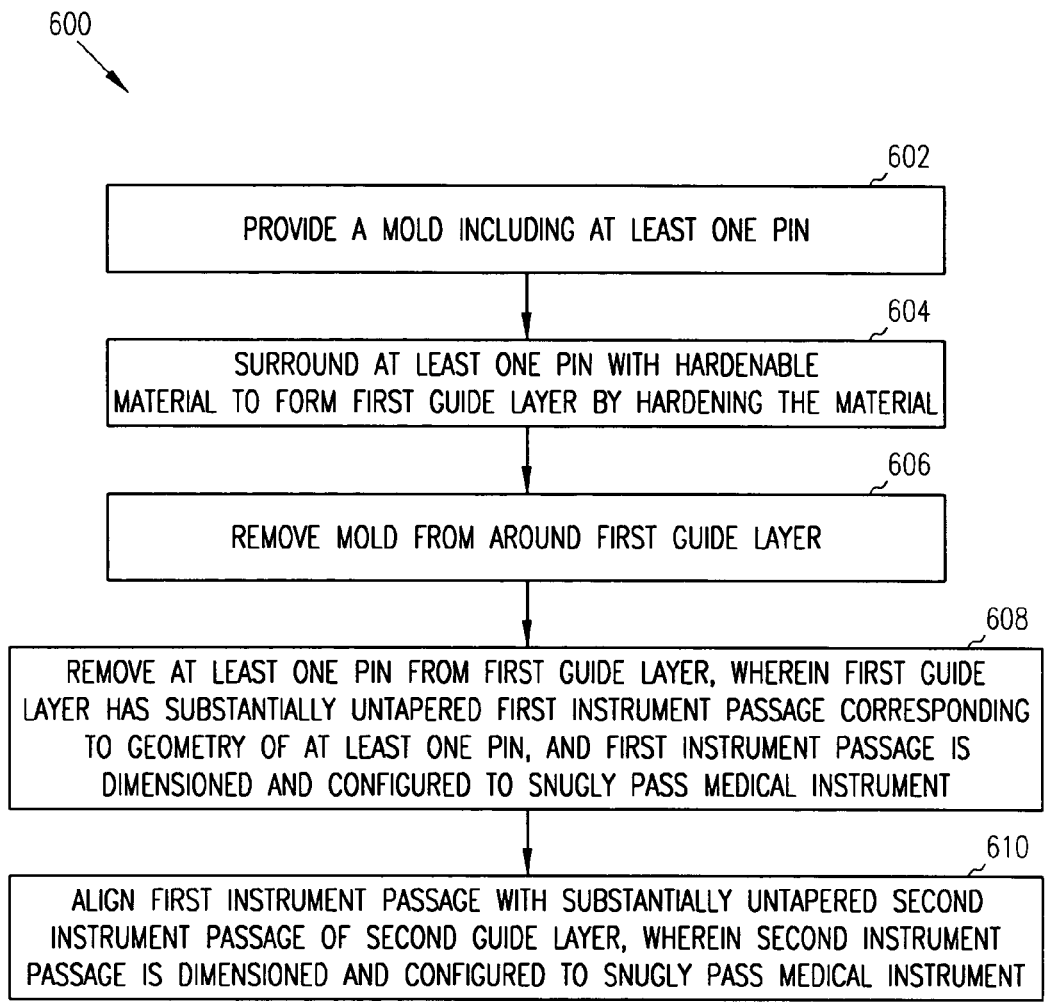
FIG. 6 is a block diagram illustrating a method for manufacturing an instrument guide.

FIG. 6 is a block diagram showing a method of manufacture 600. As shown in block 602, at least a mold having at least one pin is provided. In an example, the pin has a substantially untapered outer perimeter sized and shaped to correspond to the inner surface of the guide layer 102 that defines the substantially untapered instrument passage 204 and channels 206A-E. As shown in block 604, the pin is then surrounded with a hardenable material, such as Grilamid®, polycarbonate, injection molded plastics, epoxies or the like. This material hardens (i.e., solidifies) to form the first guide layer 102. Then, in block 606, the mold is broken away or otherwise removed from around the first guide layer 102. The first guide layer 102 is molded in substantially the same shape as the inner surface of the mold. In one example, the inner surface of the mold substantially corresponds to the outer perimeter of the guide layer 102. In one example, the inner surface of the mold includes at least one ridge disposed thereon. In another example, four ridges are positioned about 90 degrees around the mold inner surface. The ridges define corresponding grooves 202 on the outer perimeter of the first guide layer 102. As shown in block 608, the pin is removed from the first guide layer 102. In one example, the first guide layer 102 is pushed off of the pin. In an example, the inner surface of the first guide layer 102 corresponds to the outer surface of the pin. In other words, the first guide layer 102 includes an instrument passage 204 and corresponding channels 206A-E defined by the geometry of the pin. Because the pin has a substantially untapered outer perimeter, the instrument passage 204 and channels 206A-E correspondingly are substantially untapered. In another example, the substantially untapered passage 204 and channels 206A-E are formed by laser drilling, EDM and the like.

As shown in block 610, the first instrument passage is aligned with a second instrument passage of the first guide layer and second guide layer, respectively. In one example, the first and second instrument passages are sized and shaped to snugly pass a medical instrument. In another example, the first guide layer 102 is positioned within a guide coupler, for example guide coupler 104. Optionally, the first guide layer 102 is disposed within the guide layer lumen 108, and the guide layer 102 is sized and shaped to snugly fit within the guide coupler 104. In one example, the first guide layer 102, including at least one groove 202, is positioned within the guide coupler 104 so at least one ridge 107 is disposed within the groove 202. In still another example, a second guide layer 102 is then positioned within the guide coupler 104. Optionally, the second guide layer 102 includes a substantially untapered instrument passage 204 and associated channels 206A-E. The channels 206A-E of the second guide layer 102 are aligned with those of the first guide layer 102. In one option, the second guide layer 102 includes a groove 202, such that the ridge 107 is disposed within the groove 202 of the second guide layer 102. This aligns the instrument passage 204 and channels 206A-E of the first and second guide layers 102.

In still another example, the first guide layer 102 is adhered to the second guide layer 102 and/or the guide coupler 104. The guide layers 102 are affixed with adhesives, ultrasonic bonding, snaps, press pins, screws and the like. The top guide layer 102 and bottom guide layer 102 are adhered to the guide coupler 104, for instance, with an adhesive including cyanoacrylate. In yet another example, the guide layers 102 are interference fit with the guide coupler 104. Optionally, additional guide layers 102 are disposed within the guide coupler 104 to define extended passages through aligned channels 206A-E. With additional guide layers 102, the top guide layer 102 and the bottom guide layer 102 retain the additional guide layers 102 within the guide coupler 104.

The various embodiments of the instrument guide and method for making the same in this document are presented as illustrative examples, and are not intended to be limiting. The instrument guide embodiments discussed in this document will be capable of use with a variety of instruments including sensing and stimulation electrodes, catheters, biopsy probes or the like. The instrument guide includes substantially untapered channels that allow snug coupling between the channels and instruments. In another example, the untapered channels allow snug coupling between the channels and tubes interposed between the channels and the instruments. In still another example, the substantially untapered channels provide snug slidable coupling between long, thin instruments and tubes.

Moreover, providing multiple aligned guide layers defines substantially untapered elongated passages that accurately track instruments fed therethrough. The tight tolerance between the inner diameter of the guide layers and the outer diameter of the instrument enhances the accuracy of guidance for the instrument while still allowing slidable movement. Accurate placement of the instrument is achieved where the instrument is aligned to a desired trajectory and maintained on the desired trajectory during plunging. Because the substantially untapered passage provides an elongated passage with a tight tolerance to the instrument, the instrument is precisely plunged into the brain, for instance, even after the instrument exits the elongated passage. As a result, a plunged instrument fed through the substantially untapered passage of the instrument guide remains parallel and coincident to a desired trajectory.

Making an instrument guide with an elongate passage without stacking guide layers requires, in one example, tapering of the channel with a correspondingly tapered molding pin. When the channel is not tapered removal of the pin often distorts the channel because the pin is drawn over a relatively long distance. Tapering of the channel helps avoid distortion as the tapered pin is drawn along the channel a shorter distance. However, the resulting tapered channel less accurately tracks instruments disposed therein because its proximal portion is less snugly fit to the instrument. As a result of the excessive clearance between the instrument and the proximal portion of the instrument guide the instrument tracks less accurately. Additionally, where it is desirable to have closely packed elongate passages, for instance in image guided surgery, using tapered channels undesirably spaces the channels from each other.

Alternatively, molding is performed around adjacent guide tube liners. As described above, in an example where the instrument guide is used in image guided surgery it is desirable to have closely packed elongate passages. Using tube liners undesirably spaces the passages from each other. Moreover, elongate passages are also drilled. However, when multiple closely spaced elongate passages are desired a drill bit can move or 'wander,' and break into the nearby passages.

In the method disclosed herein, when drawing the untapered pin through a guide layer the drawn distance is relatively short allowing for a substantially untapered lumen and corresponding channels. In one example, this distance is the thickness of the first layer, which is less than about a quarter of an inch. The instrument guide thus provides elongate substantially untapered passages defined by the channels of stacked guide layers.

In another example, an instrument guide having passages angled with respect to a longitudinal center axis of the instrument guide is made using the techniques described herein. In one example, separate molds are provided for each guide layer of the angled instrument guide. The separate molds include angled pins disposed within the molds. In another example, the pins are integral to the molds. The pins are selectively oriented within each mold so guide layers formed from the molds provide continuous substantially untapered and angled passages when the channels of each guide layer are aligned. In other words, the pin position within each mold is varied so that when the guide layers are stacked an angled continuous substantially untapered passage is formed. One example of an instrument guide having angled passages is further described in U.S. patent application Ser. No. 10/370,090, filed on Feb. 20, 2003, which is assigned to the assignee of the present application and which is incorporated by reference herein in its entirety.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the invention should, therefore, be determined with reference to the appended claims, along with the full scope of equivalents to which such claims are entitled.

What is claimed is:

1. An article of manufacture comprising:
an instrument guide formed by a plurality of separate and identical guide layers defining a longitudinal guide passage for guiding a surgical instrument to access an anatomic target site, the plurality of guide layers including at least:
a first guide layer including a substantially untapered and non-threaded first instrument passage;
a second guide layer identical to the first guide layer, the second guide layer including a substantially untapered and non-threaded second instrument passage, wherein the second instrument passage is aligned with the first instrument passage, and wherein the second guide layer is removably stacked atop the first guide layer and in contact with the first guide layer, wherein each of the first and second instrument passages defines a central channel and a plurality of channels surrounding the central channel, the central passage and each of the surrounding channels of the first and second guide layers aligned for providing uninterrupted access to the anatomic target site; and
an elongated guide coupler having first and second open ends, the guide coupler having an inner surface defining a guide layer lumen through the first and second ends, the guide layer lumen sized and shaped to stackably receive the first and second guide layers.

2. The article of manufacture of claim 1, wherein the at least two or more channels are substantially parallel to each other.

3. The article of manufacture of claim 1, wherein the plurality of surrounding channels includes four surrounding channels circumferentially surrounding the central channel at 90 degree increments, each of the four surrounding channels open to and communicating with the central channel.

4. The article of manufacture of claim 1, wherein the first guide layer and second guide layer include polyamide.

5. The article of manufacture of claim 1, wherein the guide coupler includes at least one longitudinal ridge disposed along the inner surface of the guide coupler, and wherein each of the first and second guide layers includes an outer surface with at least one longitudinal groove, and the longitudinal ridge disposed within at least one corresponding longitudinal groove of each of the the first and second guide layers.

6. The article of manufacture of claim 5, further including a plurality of parallel longitudinal ridges and a plurality of corresponding parallel longitudinal grooves.

7. The article of manufacture of claim 6, wherein the inner surface of the guide coupler is substantially cylindrical and the plurality of parallel longitudinal ridges includes four longitudinal ridges with a triangular cross-sectional geometry equally spaced about the inner surface of the guide coupler.

8. The article of manufacture of claim 7, wherein the outer surfaces of the first guide layer and the second guide layer are substantially cylindrical and sized and shaped to snugly fit within the inner surface of the guide coupler and the plurality of longitudinal grooves includes four triangularly shaped longitudinal grooves equally spaced about the outer surfaces.

9. The article of manufacture of claim 1, wherein the guide layer lumen is substantially aligned with a longitudinal center axis of the guide coupler.

10. The article of manufacture of claim 1, wherein the guide layer lumen is substantially parallel to a longitudinal center axis of the guide coupler and offset from the longitudinal center axis.

11. The article of manufacture of claim 1, further comprising a translatable stage coupled to the guide coupler, wherein the translatable stage includes a first stage moveably coupled to a base and a second stage moveably coupled to the first stage.

12. The article of manufacture of claim 11, wherein at least a portion of the guide coupler is disposed within an orifice in the base, the guide coupler including a plurality of keys on an outer surface for keyed coupling to the base.

13. The article of manufacture of claim 11, wherein the first stage and the second stage are moveable substantially parallel to the substantially untapered first instrument passage and the second instrument passage.

14. The article of manufacture of claim 1, further comprising a trajectory guide coupled to the guide coupler, wherein the trajectory guide includes a base ring, a rotatable base moveably coupled to the base ring and a saddle slide moveably coupled to an arcuate surface of the rotatable base.

15. The article of manufacture of claim 14, wherein at least a portion of the guide coupler is disposed within the saddle slide.

16. The article of manufacture of claim 1, wherein the first guide layer and the second guide layer are cylindrical.

17. An article of manufacture comprising:
an instrument guide defining a longitudinal axis and a longitudinal guide passage along the longitudinal axis for guiding a surgical instrument to access an anatomic target site, the instrument guide including:
a plurality of separate and substantially identical guide layers, each guide layer including a substantially untapered and non-threaded instrument passage, the guide layers stackable in contact with one another to form a continuous stack of a selectable number of guide layers, such that the instrument passages of all the guide layers are aligned along the longitudinal axis and define the longitudinal guide passage, wherein each instrument passage includes a central channel and a plurality of surrounding channels circumferentially surrounding the central channel, the central passage and each of the surrounding channels providing uninterrupted access to the anatomic target site, and wherein the surrounding channels are interconnected and are open to and communicate with the central channel; and
an elongated guide coupler having first and second open ends, the elongated guide coupler having an inner surface defining a guide layer lumen through the first and second ends, the guide layer lumen sized and shaped to slidably receive the continuous stack of the plurality of guide layers.

18. The article of manufacture of claim 17, wherein the guide coupler includes an upper portion, a lower portion and a flange interposed between the upper portion and the lower portion, the upper portion having a smaller outer perimeter than the lower portion, the flange having an outer perimeter greater than that of the upper portion and the lower portion.

19. The article of manufacture of claim 18, wherein the upper portion has longitudinal axis parallel to and offset from a longitudinal axis of the lower portion.

20. The article of manufacture of claim 18, wherein the flange extends part way around the guide coupler.

21. The article of manufacture of claim 18, further comprising a translating stage coupled to the guide coupler, the translating stage defining an orifice, and wherein the upper portion includes a plurality of keys disposed around an outer perimeter of the upper portion, the plurality of keys engageable with the orifice.

22. The article of manufacture of claim 18, wherein the upper portion includes a recess extending circumferentially around an outer perimeter of the upper portion.

23. The article of manufacture of claim 18, wherein the lower portion includes a recess extending circumferentially around an outer perimeter of the lower portion.

24. The article of manufacture of claim 18, wherein each guide layer has a cylindrical outer surface and wherein the guide layer lumen of the guide coupler has a cylindrical inner surface, wherein the inner and outer surfaces include cooperating alignment ridges and grooves respectively.

25. The article of manufacture of claim 17, wherein the plurality of guide layers includes at least ten guide layers.

26. An article of manufacture comprising:
an instrument guide defining a longitudinal axis and a longitudinal guide passage along the longitudinal axis for guiding a surgical instrument to access an anatomic target site, the instrument guide including:
a plurality of separate and substantially identical guide layers, each guide layer including a substantially untapered and non-threaded instrument passage, the guide layers stackable in contact with one another to form a continuous stack of a selectable number of guide layers, such that the instrument passages of all the guide layers are aligned along the longitudinal axis and define the longitudinal guide passage, wherein each instrument passage includes a central channel and a plurality of surrounding channels circumferentially surrounding the central channel, the central passage and the surrounding channels providing uninterrupted access to the anatomic target site, and wherein the surrounding channels are interconnected and are open to and communicate with the central channel, and wherein each guide layer has a cylindrical outer surface and a plurality of longitudinal grooves formed on the cylindrical outer surface; and an elongated guide coupler having first and second open ends, the guide coupler having a cylindrical inner surface defining a guide layer lumen through the first and second ends, the inner surface defining a plurality of longitudinal ridges, the guide layer lumen sized and shaped to receive the continuous stack of separate guide layers such that each longitudinal ridge is received in a corresponding groove of each guide layer, the guide coupler including an upper portion, a lower portion and a flange interposed between the upper portion and the lower portion, the upper portion having a smaller outer perimeter than the lower portion, the flange having an outer perimeter greater than that of the upper portion and the lower portion, the lower portion having a longitudinal axis parallel to and offset from a central longitudinal axis of the guide layer lumen.

27. The article of manufacture of claim 26, wherein the plurality of longitudinal ridges includes four longitudinal ridges having triangular cross-sections and equally spaced about the inner surface.

28. The article of manufacture of claim 26, wherein the plurality of guide layers includes at least ten guide layers.

* * * * *